(12) United States Patent
Pinkhassik et al.

(10) Patent No.: US 7,829,155 B1
(45) Date of Patent: Nov. 9, 2010

(54) NANOTHIN POLYMER COATINGS CONTAINING THIOL AND METHODS OF USE THEREOF

(75) Inventors: Evgueni Pinkhassik, Memphis, TN (US); Larry Todd Banner, Cordova, TN (US); Benjamin T. Clayton, Pikeville, TN (US)

(73) Assignee: The University of Memphis Research Foundation, Memphis, TN (US)

( * ) Notice: Subject to any disclaimer, the term of this patent is extended or adjusted under 35 U.S.C. 154(b) by 558 days.

(21) Appl. No.: 11/871,669

(22) Filed: Oct. 12, 2007

Related U.S. Application Data

(60) Provisional application No. 60/867,027, filed on Nov. 22, 2006.

(51) Int. Cl.
*C08J 7/18* (2006.01)
*C08J 3/28* (2006.01)
*C08F 2/46* (2006.01)
*C07C 381/00* (2006.01)
*C08F 12/30* (2006.01)

(52) U.S. Cl. ............ 427/507; 522/81; 522/180; 427/496; 427/506; 427/508; 427/512; 427/517; 427/518; 427/520; 427/256; 427/287; 427/407.1; 427/409; 428/411.1; 428/419; 428/457; 428/461; 428/463; 568/67; 568/68; 568/77; 526/286; 264/426; 264/446; 264/448; 264/458; 264/405; 264/494; 264/496; 585/400; 585/411; 585/435; 585/436; 585/437; 585/440

(58) Field of Classification Search ............ 568/67, 568/68, 77; 526/286; 522/180, 81; 428/411.1, 428/419, 457, 461, 463; 585/400, 411, 435, 585/436, 437, 440; 264/405, 426, 446, 448, 264/485, 494, 495; 427/508, 512, 517, 518, 427/520, 256, 265, 287, 407.1, 409
See application file for complete search history.

(56) References Cited

U.S. PATENT DOCUMENTS

| | | | |
|---|---|---|---|
| 5,290,956 A * | 3/1994 | Emmons et al. ............ 549/478 |
| 5,382,640 A * | 1/1995 | Emmons et al. ............ 526/266 |
| 5,403,902 A | 4/1995 | Heilmann et al. |
| 5,549,931 A | 8/1996 | Dattatraya et al. |
| 5,773,581 A | 6/1998 | Camble et al. |
| 6,217,901 B1 | 4/2001 | Perrott et al. |
| 6,492,283 B2 | 12/2002 | Raaijmakers et al. |
| 6,617,173 B1 | 9/2003 | Sneh |
| 6,905,547 B1 | 6/2005 | Londergan et al. |
| 6,967,154 B2 | 11/2005 | Meng et al. |
| 7,045,430 B2 | 5/2006 | Ahn et al. |
| 2001/0016273 A1 | 8/2001 | Narasimhan et al. |
| 2001/0023250 A1 | 9/2001 | Spada et al. |
| 2003/0091609 A1 | 5/2003 | Hendriks |
| 2003/0138608 A1 | 7/2003 | Landry-Coltrain et al. |
| 2003/0157732 A1 | 8/2003 | Baker et al. |
| 2004/0058135 A1 | 3/2004 | Patel et al. |
| 2004/0121139 A1 | 6/2004 | Yim et al. |
| 2004/0202789 A1 | 10/2004 | Patil et al. |
| 2005/0175661 A1 | 8/2005 | Hunter et al. |
| 2006/0041077 A1 | 2/2006 | Kriesel et al. |
| 2010/0001264 A1 * | 1/2010 | Aramaki et al. ............ 257/40 |

FOREIGN PATENT DOCUMENTS

| | | |
|---|---|---|
| JP | 04363320 A * | 12/1992 |
| WO | WO2004007597 A1 | 1/2004 |

OTHER PUBLICATIONS

Banner et al. Self-Limiting robust Surface-Grafted Organic Nanofilms. Chemistry of Materials (2010), 22(7), 2248-2254.*

Haupt, Karsten; Mosbach, Klaus; Molecularly Imprinted Polymers and Their Use in Biomimetic Sensors; Chem. Rev.; Jun. 2000; 100; 2495-2504.

Marty, Jean Daniel; Mauzac, Monique; Molecular Imprinting: State of the Art and Perspectives; Adv. Polym. Sci.; 2005; 172; 1-35.

Li, Wuke; Li, Songjun; Molecular Imprinting: A Versatile Tool for Separation, Sensors and Catalysis; Adv. Polym. Sci.; Oct. 19, 2006; 206; 191-210.

(Continued)

*Primary Examiner*—Sanza L McClendon
(74) *Attorney, Agent, or Firm*—Peter F. Corless; Brian R. Landry; Edwards Angell Palmer & Dodge LLP

(57) ABSTRACT

The present invention provides a new monomer and methods of using the monomer to fabricate robust polymer surface coatings with controlled thicknesses between 1 and 5 nanometers. The coatings are composed of a new material containing polymerized monomers of 4-vinylbenzenepropanethiol. The polymer surface coating may be applied to metal and silicon. The method includes exposing a metal substrate to a solution of the monomer in hexanes in order to deposit a monolayer of the monomer onto the metal surface. The substrate is then irradiated with ultraviolet radiation in order to graft a thin polymer coating onto the surface. The procedure can be repeated in order to control the thickness of the coating between about 1 nm and 5 nm. Alternatively, thermally initiated polymerization or deposition of partially oligomerized monomers onto the surface provides nanothin coatings with identical performance. The coating provides complete surface coverage, is extremely robust, and exhibits excellent insulating and anti-corrosive properties.

14 Claims, 12 Drawing Sheets

OTHER PUBLICATIONS

Gorteau, Virginie; Bollot, Guillaume; Mareda, Jiri; Pasini, Dario; Tran, Duy-Hien; Lazar, Adina N., Coleman, Anthony W.; Sakai, Naomi; Matile, Stefan; Synthetic multifunctional pores that open and close in response to chemical stimulation; Bioorganic & Medicinal Chemistry 13; Jun. 2005; 5171-5180.

Bayley, H.; Martin, C.R. Resistive-Pulse Sensing—From Microbes to Molecules; Chem. Rev.; Jun. 21, 2000, 100, 2575-2594.

Kasianowicz, J.J.; Brandin, E.; Branton, D.; Deamer, D.W. Char. of Ind. Polynucleotide Molecules Using a Membrane Channel; Proc. Natl. Acad. Sci. U.S.A.; Nov. 1996, 93, 13770-13773.

Alper, J. From the Bioweapons Trenches, New Tools for Battling Microbes; Science; Jun. 11, 1999, 284, 1754-1755.

Vriezema, D.M.; Aragones, M.C.; Elemans, J.A.A.W.; Cornelissen, J.J.L.M.; Rowan, A.E.; Nolte, R.J.M. Self-Assembled Nanoreactors; Chem. Rev. Mar. 1, 2005, 105, 1445-1489.

Nardin, C.; Thoeni, S.; Widmer, J.; Winterhalter, M.; Meier, W. Nanoreactors based on (polymerized) ABA-triblock copolymer vesicles; Chem. Commun. The Royal Society of Chemistry 2000, 1433-1434.

Lin, Z., Kim, D. H., Wu, X., Boosahda, L., Stone, D., Larose, L. & Russell, T. P. A Rapid Route to Arrays of Nanostructures in Thin Films; Advanced Materials Oct. 2, 2002, 14, 1373-1376.

Jeong, U.; Ryu, D. Y., Kim, J. K., Kim, D. H., Wu, X. & Russell, T. P. Precise Control of Nanopore Size in Thin Film Using Mixtures of Asymmetric Block Copolymer and Homopolymer; Macromolecules Dec. 2, 2003, 36, 10126-10129.

Wei, Y.; Qiu, K.-Y. A Novel Nonsurfactant Route to Nanoporous Materials and Its Biological Applications; Series on Chemical Engineering, Nanoporous Materials; 2004, vol. 4; Ch. 28; 873-892; Imperial College Press.

Desai, T.A.; Hansford, D.J.; Kulinsky, L.; Nashat, A.H.; Rasi, G.; Tu, J.; Wang, Y.; Zhang, M.; Ferrari, M.; Nanoporous anit-fouling silicon mebranes for biosensor applications; Biosensors & Bioelectronics 2000, 15, 454-462.

Poulain, N.; Nakache, E.; Pina, A.; Levesque, G.J. Nanoparticles from Vesicle Polymerization: Characterization and Kinetic Study; Journal of Polymer Science 1996, 34, 729-737.

Hotz, J.; Meier, W. Vesicle-Templated Polymer Hollow Spheres; Langmuir Feb. 3, 1998, 14, 1031-1036.

Nardin, C. Hirt, T.; Leukel, J.; Meier, W. Polymerized ABA Triblock Copolymer Vesicles; Langmuir, Nov. 20, 1999, 16, 1035-1041.

Kurja, J.; Noelte, R.J.M.; Maxwell, I,A,; German, A,I, Free Radical Polymerization of Styrene in Dioctadecyldimethylammonium Bromide Vesicles; Polymer, 1993, 34, 2045-2049.

McKelvey, C.A.; Kaler, E.W.; Zasadzinski, J.A.; Coldren; Jung, H.T. Templating Hollow Polymeric Spheres from Catanionic Equilibrium Vesicles: Synthesis and Characterization; Langmuir, Sep. 28, 2000, 16, 8285-8290.

Jung, M.; Hubert, D.H.W.; Bomans, P.H.H.; Frederik, P.M.; Meuldijk, J.; Van Herk, A.M.; Fischer, H. German, A.I. New Vesicle-Polymer Hybrid: the Parachute Architecture; Langmuir 1997, 13, 6877-6880.

McIntosh, T. J., Simon, S. A. & MacDonald, R. C. The Organization of n-Alkanes in Lipid Bilayers; Biochimica et Biophysica Acta 1980, 597, 445-463.

McDaniel, R. V., Simon, S. A., McIntosh, T. J. & Borovyagin, V. Interaction of Benzene with Bilayers. Thermal and Structural Studies; Biochemistry 1982, 21, 4116-4126.

Kitiyanan, B., O'Haver, J. H., Harwell, J. H. & Osuwan, S. Absolubilization of Styrene and Isoprene in Cetyltrimethylammonium Bromide Admicelle on Precipitated Silica; Langmuir 1996, 12, 2162-2168.

Well, A., Dechenaux, E. The Spin-Coating Mechanism Related to Polymer Solution Properties; Polymer Engineering and Science, Mid-Aug. 1988, 28, 15, 945-948.

Dyer, D.J., Feng, J., Schmidt, R., Wong, V.N., Zhoa, T., Yagci, Y. Photoinduced Plymerization from Dimethylamino-Terminated Self-Assembled Monolayers on Gold; Macromolecules 2004, 37, 7072-7074.

* cited by examiner

Figure 8

| Substrate ID | Initial (Å) | After Vortexing (Å) | After Rubbing (Å) |
|---|---|---|---|
| 1 | 52.0 | 51.6 | 46.8 |
| 2 | 46.5 | 46.7 | 46.2 |

Figure 9

| Deposition Time (hours) | Thickness (Å) by Ellipsometry |
|---|---|
| 0.5 | 20.2 ± 0.8 |
| 2.0 | 24.3 ± 0.7 |
| 3.0 | 34.7 ± 0.5 |
| 18.0 | 45.7 ± 0.7 |
| 41.0 | 40.3 ± 0.7 |

Figure 10

| Solvent | Thickness (Å) by Ellipsometry |
|---------|-------------------------------|
| None    | 36.7 ± 5.4                    |
| Hexanes | 37.6 ± 9.2                    |
| Toluene | 34.6 ± 1.9                    |
| Ethanol | 36.8 ± 2.4                    |
| 1M KCl  | 37.2 ± 2.7                    |

NANOTHIN POLYMER COATINGS CONTAINING THIOL AND METHODS OF USE THEREOF

This application claims the benefit of U.S. Provisional Patent Application No. 60/867,027, filed Nov. 22, 2006, entitled "Nanothin Polymer Coatings Containing Thiol and Methods of Use Thereof," which is hereby incorporated by reference in its entirety.

Be it known that, we, Evgueni Pinkhassik, a citizen of Russia, residing at 258 Betty Jo Lane, Memphis, Tenn. 38117; Larry Todd Banner, a citizen of the United States, residing at 1678 North Frence Creek Cove, Cordova, Tenn. 38016; and Benjamin Clayton, a citizen of the United States, residing at Route 1 Box 195 Pikeville, Tenn. 37367, have invented new and useful "Nanothin Polymer Coatings Containing Thiol and Methods of Use Thereof".

STATEMENT REGARDING FEDERALLY SPONSORED RESEARCH OR DEVELOPMENT

This invention was made with federal grant money under NSF grant CHE-0349315. The United States Government has certain rights in this invention.

REFERENCE TO A "MICROFICHE APPENDIX"

Not applicable

FIELD OF THE INVENTION

The present invention relates to a new polymer used in the production of a polymerization coating. The polymerization coating is used to coat metals, and other substances, in order to provide protection from corrosion and insulation.

BACKGROUND OF THE INVENTION

Surface coatings play a major role in our lives. They include paints, adhesives, and sealants, among many others. They are often used for decoration and protection of surfaces. These coatings typically utilize properties of adhered films with bulk thicknesses. With reference to metals, corrosion is deterioration of essential properties in a material due to reactions with its environment. In metals and metal alloys, corrosion begins with the loss of an electron and is described as an electrochemical process (Jones, Denny, 1996, *Principles and Prevention of Corrosion,* 2nd edition, Upper Saddle River, N.J., Prentice Hall, ISBN 0-13-359993-0). Existing coatings, such as traditional paints and polymer coatings typically have thickness measured in tens of microns to ensure complete coverage of the metal surface and adequate adhesion properties. Due to the importance of coatings, significant efforts have been devoted to fabricate them with thicknesses less than 100 micrometers. Common thin film fabrication methods include spin-coating and polymer brushes. Spin-coating (Weill, A. & Dechenaux, E., 1998, The spin-coating process mechanism related to polymer solution properties. *Polymer Engineering and Science* 28, 945-948) can reliably create films with thicknesses down to 200 nm while polymer brushes are useful for growing films that are about 10-500 nm thick (Dyer, D. J., Feng, J., Schmidt, R., Wong, V. N., Zhao, T. & Yagci, Y., 2004, Photoinduced polymerization from dimethylamino-terminated self-assembled monolayers on gold. *Macromolecules* 37, 7072-7074). Such bulky thickness is not practical when coatings are needed in confined spaces and the chemical components of such coatings may leach out of the coating into the environment. Accordingly, there is a need for nanothin insulating robust coatings to address these issues and provide a superior corrosion protection.

SUMMARY OF THE INVENTION

This invention describes a new method for preparing soft nanothin films with thicknesses between 1 nm and 5 nm. As thicknesses increase above 1 nm the materials' properties change from two dimensional to three dimensional. Films with thicknesses between 1 nm and 10 nm are of interest because they are extremely thin (on a molecular level), but retain three dimensional properties. The method also results in the fabrication of a new material that can cover an entire surface. Even though its thickness is extremely small, the coating has excellent insulating properties. In theory, such films could be useful for applications in chemical sensors, nano-insulators, and molecular electronics.

Embodiments of the present invention include a compound of 4-vinylbenezenepropanethiol, a polymer thereof, and methods of use thereof. Disclosed herein is a method of making 4-vinylbenezenepropanethiol. Also disclosed herein is a method of applying that compound to a metal. That method includes providing 4-vinylbenezenepropanethiol as a solution in an organic solvent, providing a metal, placing the metal in the solution of 4-vinylbenzenepropanethiol so that the solution is in contact with the metal surface, and exposing the mixture to ultraviolet radiation. In certain embodiments, exposing the mixture to ultraviolet radiation further includes exposing the mixture to ultraviolet radiation having a wavelength of from about 200 nanometers to about 300 nanometers for a duration of from about 10 minutes to about 1 hour. In other embodiments, the ultraviolet radiation has a wavelength of about 255. In certain embodiments, the metal may be copper, gold, platinum, or iron. Another embodiment of the method of applying a compound to a metal, includes providing 4-vinylbenzenepropanethiol, providing a metal in hexane, placing the 4-vinylbenzenepropanethiol in the hexane with the metal in order to prepare a mixture, adding a thermal free radical initiator such as benzoyl peroxide to the mixture, and incubating the mixture at from about 50 degrees Celsius to about 90 degrees Celsius. In certain embodiments, incubating the mixture is from about 15 minutes to about 24 hours. In certain embodiments, the thermal free radical initiator is benzoyl peroxide. Still another embodiment for applying a compound to metal includes providing 4-vinylbenzenepropanethiol, exposing the 4-vinylbenzenepropanethiol to air at room temperature for from about 30 minutes to about 24 hours, diluting the 4-vinylbenzenepropanethiol and its oligomers in an organic solvent to about 1% w/w, and contacting the metal with the solution of 4-vinylbenzenepropanethiol and its oligomers. In certain embodiments, the method further includes incubating the metal in the solution of 4-vinylbenzenepropanethiol for from about 10 seconds to about 40 hours. In certain other embodiments, incubating the metal in the solution of 4-vinylbenzenepropanethiol for from about 10 seconds to about 30 minutes.

Also disclosed herein is a method of making 4-vinylbenzenepropanethiol. The method includes providing 1-bromo-3-phenylpropane, adding acetic anhydride and aluminum chloride, incubating the mixture at from about −20 to about 20 degrees Celsius for from about 1 hour to about 12 hours, isolating the resulting p-(3-bromopropyl)acetophenone, adding sodium borohydride to the p-(3-bromopropyl)acetophenone solution in methanol, incubating the mixture at about 0 degrees Celsius for about 2 hours, isolating the resulting p-(3-bromopropyl)-α-methylbenzenemethanol, adding toluensulfonic acid to the solution of p-(3-bromopropyl)-α-methylbenzenemethanol in toluene, refluxing the mixture under inert atmosphere for about 4 hours, isolating the resulting p-(3-Bromopropyl)styrene, adding thiourea to the p-(3-Bromopropyl)styrene, gently refluxing the mixture for about 16 hours, adding sodium hydroxide, and gently refluxing the mixture for about 4 hours.

This invention describes a nanothin polymer coating produced by either graft-to or graft from methods. Organic molecules containing both thiol and vinylbenzene functional groups, exemplified by newly synthesized 4-vinylbenzenepropanethiol, form robust coating on such metal surfaces as gold and copper with the controlled thickness in the 1-10 nm range. These coatings provide complete coverage of metal surface, act as insulators in electrochemical reactions, and are capable of preventing corrosion.

BRIEF DESCRIPTION OF THE DRAWINGS

FIG. 7 demonstrates the enhanced insulation characteristics of the polymerization coating disclosed herein as compared to the insulation capacity of monolayer of dodecanethiol.

FIG. 8 is a table showing the thickness of polymerization coatings after mechanical stripping or manipulation.

FIG. 9 is a table showing the increased thickness of the polymerization coating (thiol-styrene polymer film) as the incubation period of the substrate (gold) being submersed in the 1 mM 4-vinylbenzenepropanethiol increased.

FIG. 10 is a table demonstrating the stability of the polymerization coating subsequent to treatment with the named chemical for 30 minutes.

DETAILED DESCRIPTION OF THE INVENTION

The invention disclosed herein is a compound referred to as 4-vinylbenzenepropanethiol. 4-vinylbenzenepropanethiol is capable of polymerizing in order to create a polymer coating having a thickness of less than 10 nm. The polymer coating slows corrosion of metals and acts as an insulator and resister in electrochemical processes. Also disclosed herein is a method of applying 4-vinylbenzenepropanethiol to a metal substrate. When 4-vinylbenzenepropanethiol is applied to a metal, such as copper, gold, platinum, or iron, the beneficial properties described above are present. Finally, also disclosed herein is a method of making 4-vinylbenzenepropanethiol which results in an abundant amount of a high quality product.

Figure 1:
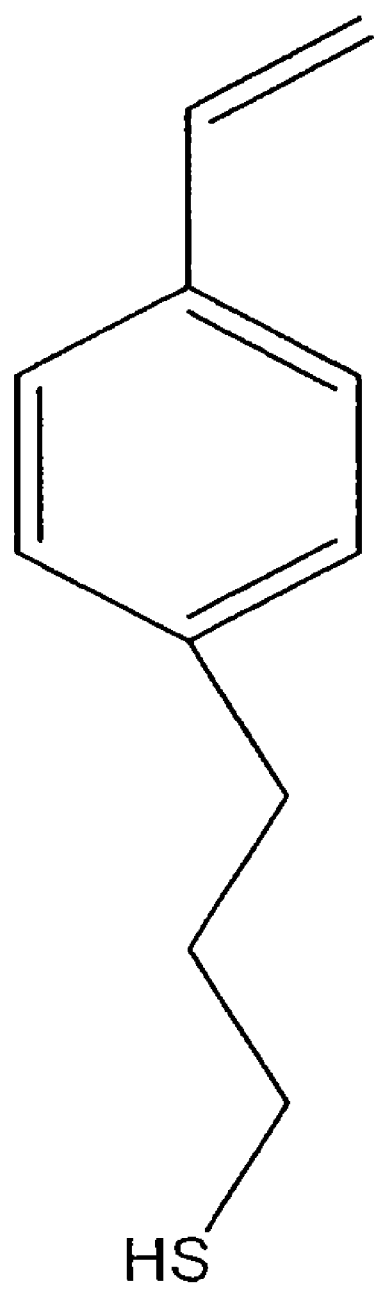
FIG. 1 is a drawing of the chemical structure of 4-vinylbenzenepropanethiol.
Figure 2:
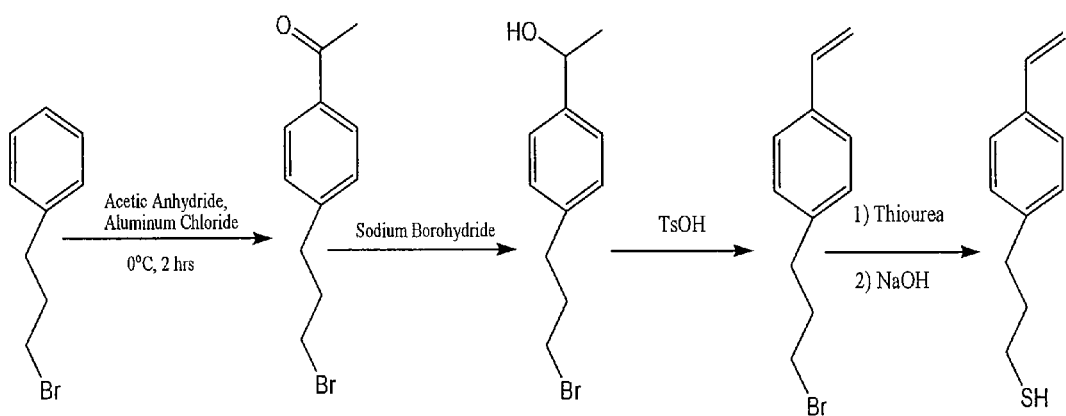
FIG. 2 is a flowchart showing the steps of synthesis to prepare 4-vinylbenzenepropanethiol from the shown starting materials.

Shown in FIG. 1, is the chemical structure of 4-vinylbenzenepropanethiol. As shown therein, the 2 functional groups, thiol and vinylbenzene (styrene), provide the characteristics necessary to allow binding to a metal surface, the formation of polymer chains, and cross-linking of those polymer chains. As further described herein, the resulting polymer coating is very thin, having a thickness of from about 1 nm to about 10 nm. Suitable metallic surfaces include metals that form bonds with thiol groups, further examples include, gold, copper, platinum, iron, silica, and the like. In certain embodiments of the present invention, the thickness of a resulting polymer coating may be from about 1 nm to about 5 nm. It is believed that the polymer coating is covalently attached to the surface of the metal. Further, the polymer coating described herein has greater chemical and mechanical stability than other self-assembled alkyl thiol monolayers. As shown below, these polymer coatings have increased insulating ability and the ability to slow corrosion of metals. A method for synthesizing 4-vinylbenzenepropanethiol is outlined in Examples 1-4 of this document. All of the starting materials described therein are widely commercially available. For example, 1-bromo-3-phenylpropane was purchased from Alfa-Aesar and was not further purified. The steps of the synthesis of 4-vinylbenzenepropanethiol are further outlined in FIG. 2.

Figure 3:
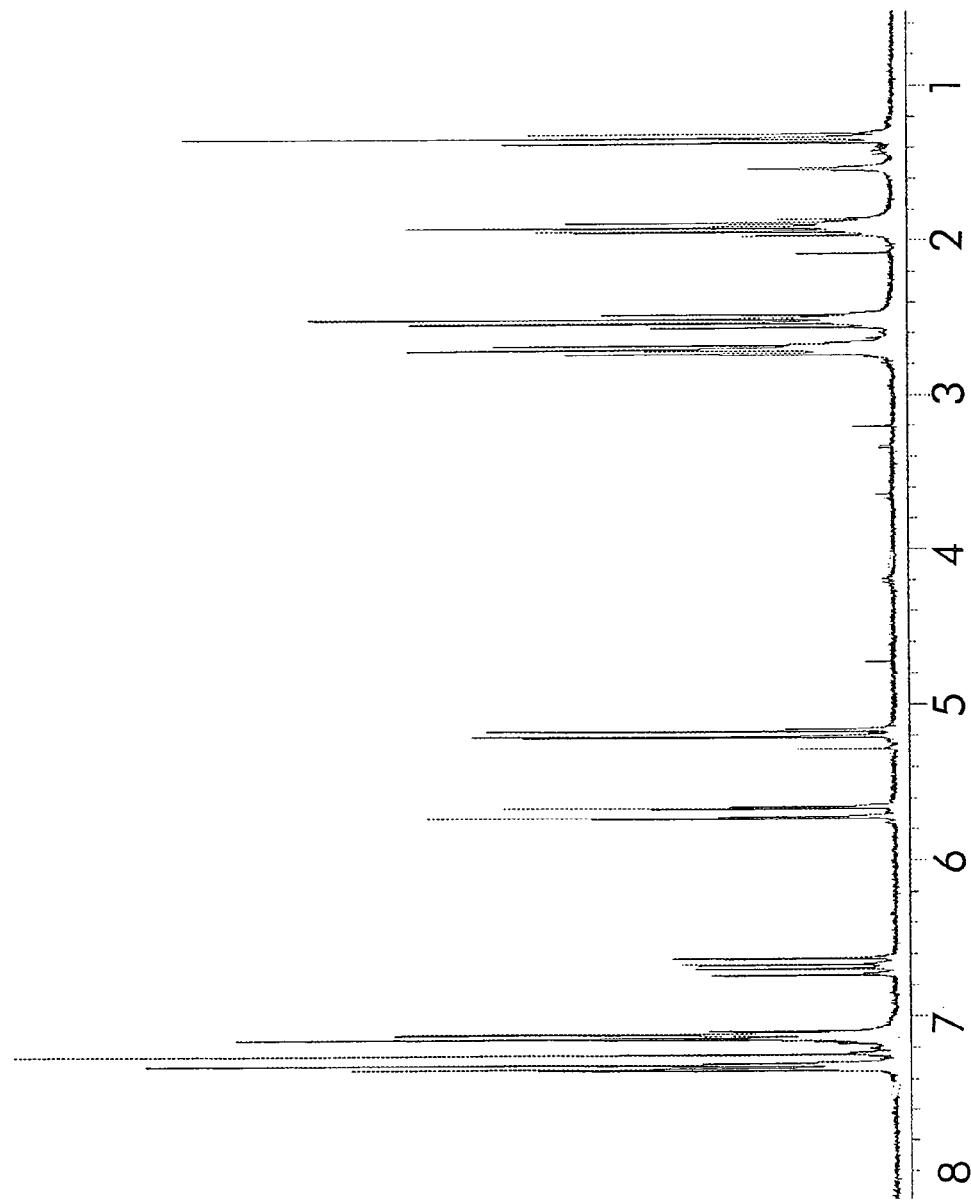
FIG. 3 is an $^1$H-NMR spectra of 4-vinylbenzenepropanethiol showing the content of the composition which results from the steps of synthesis provided herein. As shown therein $^1$H-NMR (270 MHz, CDCl$_3$) δ 1.35 (t, 1H, SH), 1.91 (m, 2H, CH2), 2.51 (m, 2H, CH2), 2.71 (t, 2H, CH2), 5.18 (d, 1 H, CH), 5.69 (d, 1H, CH), 6.68 (dd, 1H, CH), 7.13 (d, 2H, arom), 7.32 (d, 2H, arom).

Referring to FIG. 3, there is shown the $^1$H-1-NMR Septra for the 4-vinylbenzenepropanethiol which was prepared as described herein.

Figure 4:
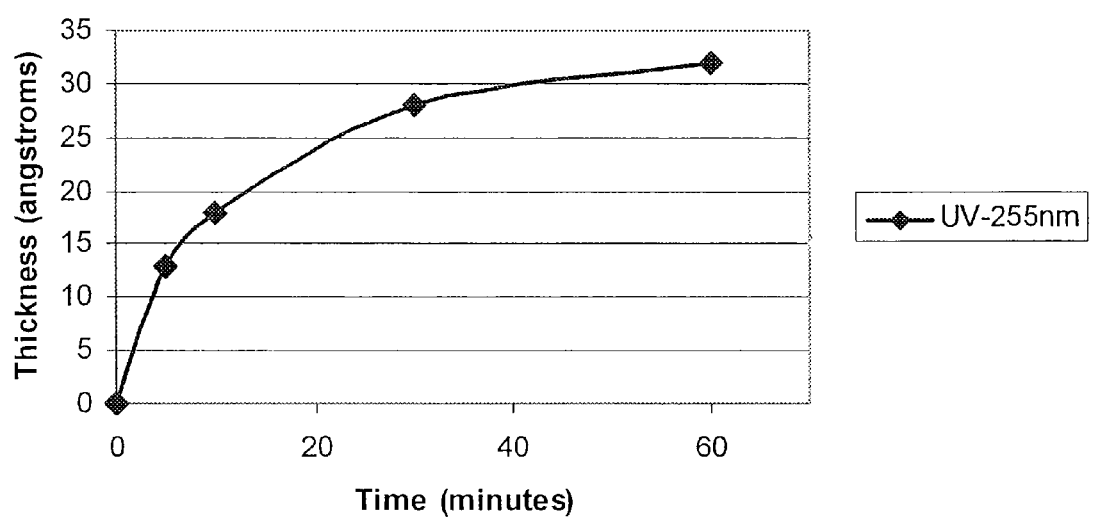
FIG. 4 is a graph of a polymer grafting from gold surface showing the increase in thickness of the polymerization coating as the incubation time of exposure to ultraviolet radiation increases. The wavelength of the ultraviolet radiation used was 255 nm.
Figure 5:
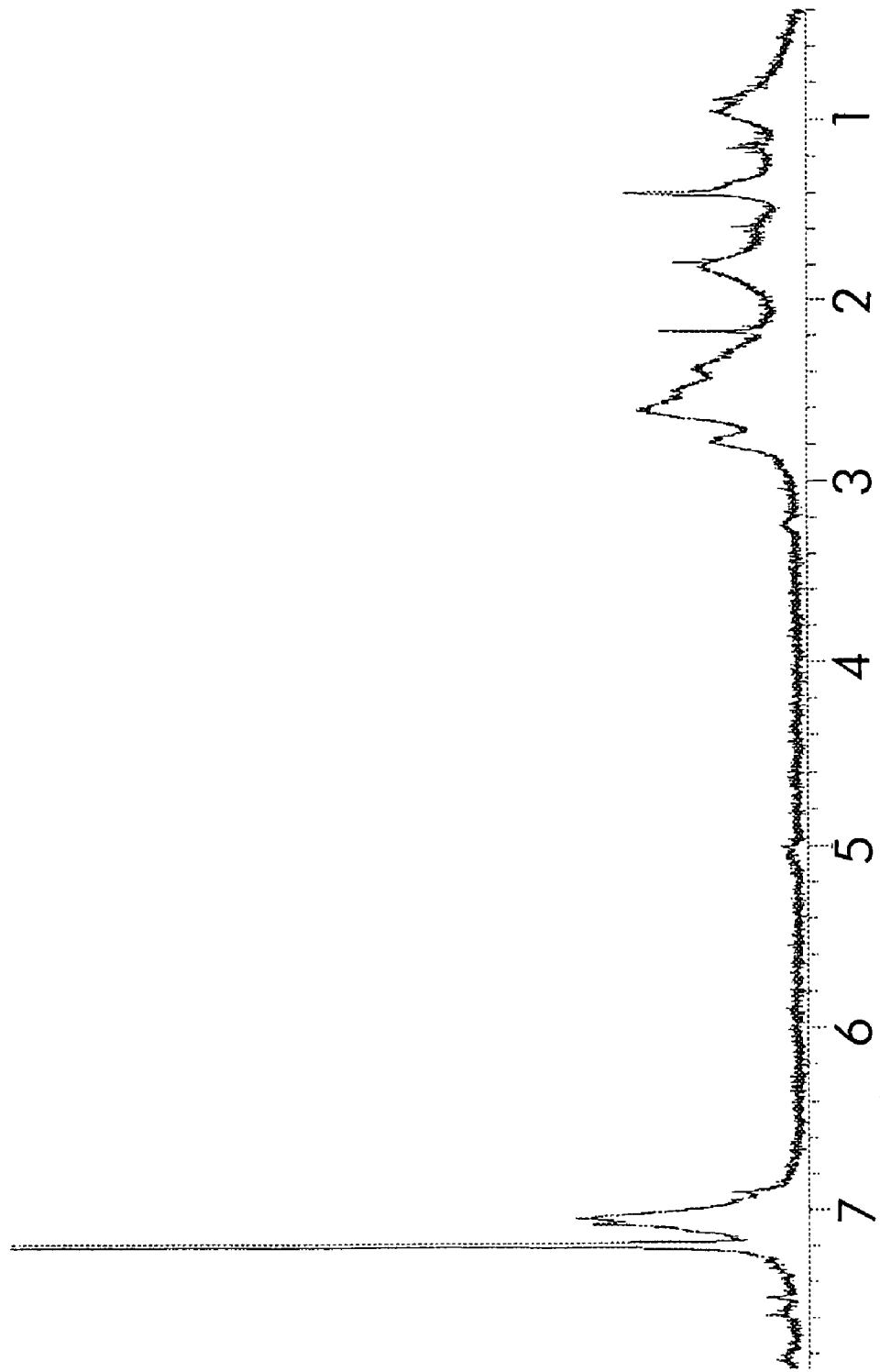
FIG. 5 is an $^1$H-NMR spectra of the polymerized coating disclosed herein. Polymerization resulted from exposure to ultraviolet radiation (255 nm) for 20 hours. The decrease in the vinyl proton peak area and increase in peak area near 2.5 ppm supports the occurrence of polymerization between vinyl and thiol groups.
Figure 6:
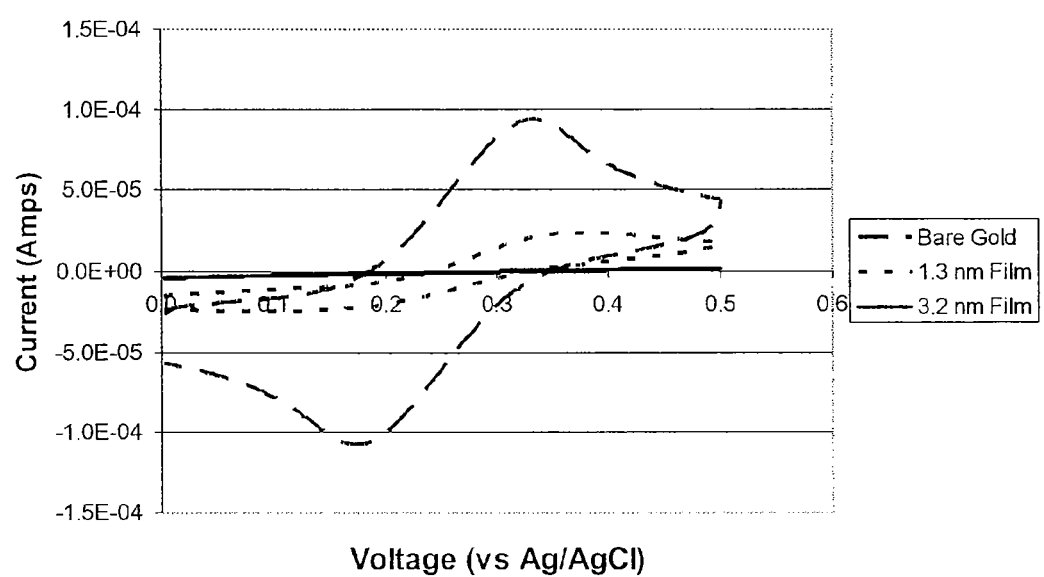
FIG. 6 demonstrates the ability of the polymerization coating to insulate the metal surface. Shown there are cyclic voltammograms using potassium ferricyanide. Shown there is a comparison between an untreated gold surface, a gold surface having a 1.3 nm polymerization coating, and a gold surface having a 3.2 nm polymerization coating. The redox mediator was 1 mM potassium ferricyanide in 1M KCl.
Figure 7A:
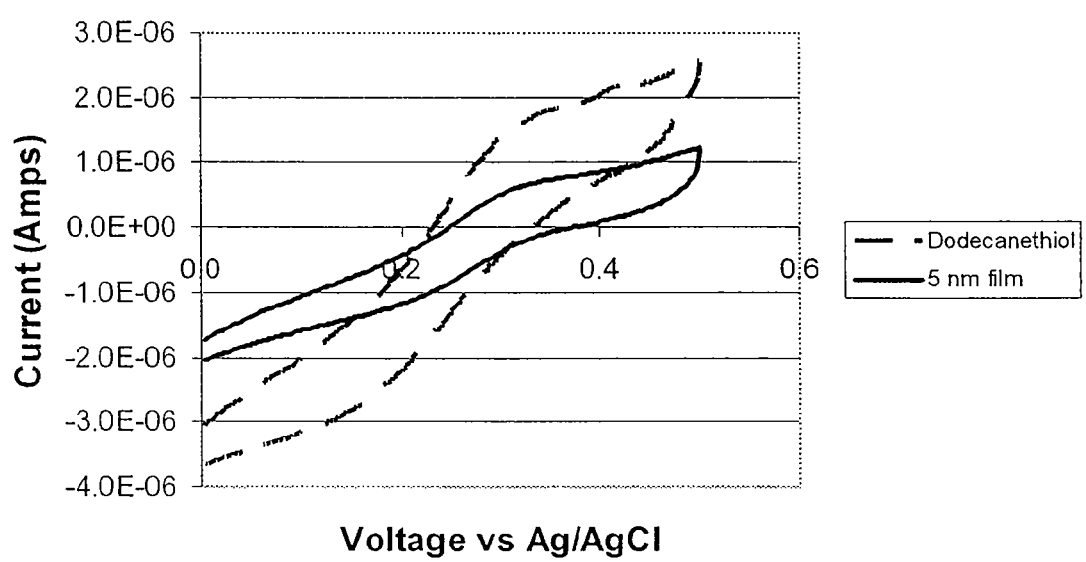
FIG. 7A is a cyclic voltammogram prior to any electrochemical stripping.
Figure 7B:
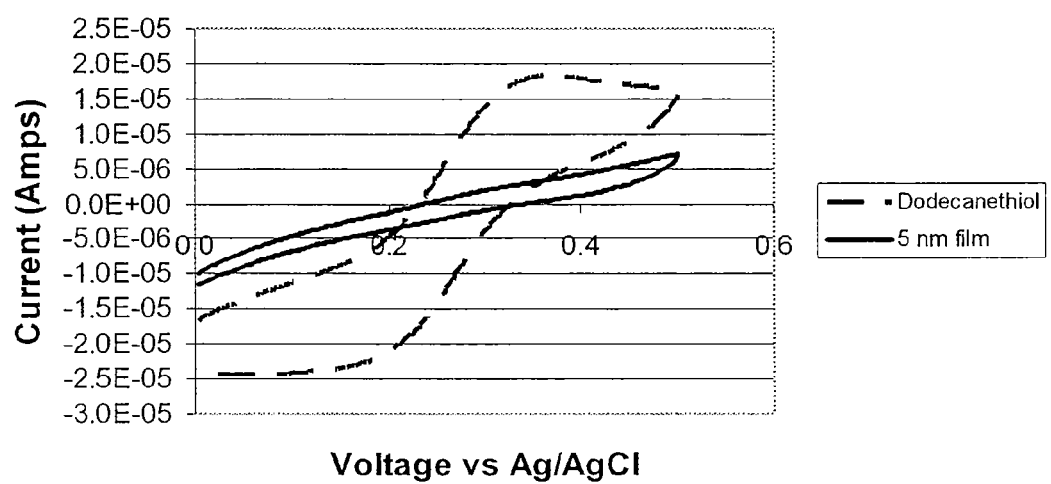
FIG. 7B is a cyclic voltammogram after 50 stripping cycles.

Disclosed herein are several methods for applying a polymer coating to a metal. One such method allows the surface polymerization of 1 mM 4-vinyl-benzenepropanethiol for gold in hexane, which results in a controlled thickness of less than 5 nm, as shown in FIG. 4. Based upon the $^1$H-NMR spectra shown in FIG. 5, thiol and vinyl functional group polymerization results after 20 hours of exposure to ultraviolet radiation. Polymerization has been demonstrated to occur with both ultraviolet light at 255 nm, and the use of thermally initiated (70-80° C. conditions using benzoyl peroxide as an initiator. The ultra thin polymerization coating described herein demonstrates the ability to provide insulation. As shown in FIG. 6, the electrical current in the redox mediator solution is nearly identical to the background electrolyte, which is the theoritical value of a completely insulated film. The redox mediator was 1 mM potassium ferricyanide in 1M KCl. As shown in FIGS. 7A and 7B, when electrochemical stripping was performed, the polymerization coating disclosed herein demonstrated enhanced stability compared to a monolayer of dodecanethiol. Specifically, electrochemical stripping was performed in 0.1 M sulfuric acid at 300 mV/second. The cyclic voltamammograms were performed in 1 mM potassium ferricyanide in 1M KCl. Finally, as shown in FIGS. 7A and 7B, the polymerization coatings demonstrated good mechanical stability. Little change in thickness was detected after the polymerization coatings had been attached to a vortexer set on high for a period of 5 minutes, nor when the coated surface of the metal was gently rubbed with a lint-free towel, as shown in FIG. 8.

Figure 11:
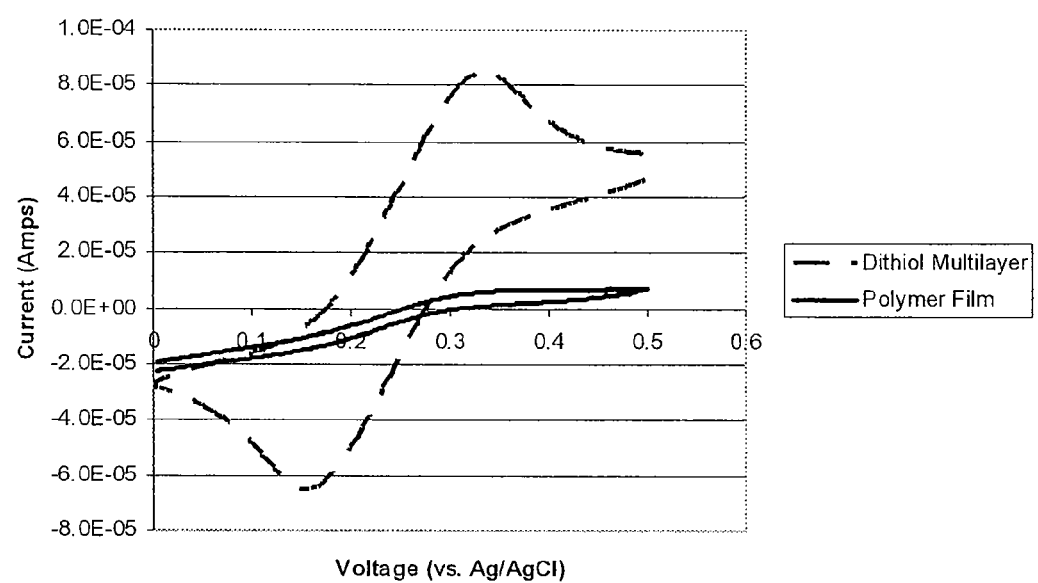
FIG. 11 shows cyclic voltammograms of electrode-mounted nanothin films, which are the named polymerization coatings, dithiol multilayer and polymer film (polymerization coating disclosed herein), to show the insulating properties. By ellipsometry, the thickness of the dithiol multilayer is 46.0±9.8 Å. The thickness of the polymer film is 45.2±0.6 Å. The redox marker is 1 mM ferrocenemethanol in 0.1 M PBS at pH=7.0 and 1 mM MgCl$_2$.

In another embodiment of the present invention, nanothin polymerization coatings with controlled thicknesses were also fabricated as follows. In this method, a metal substrate such as gold, was submersed into a hexane solution of partially polymerized 4-vinyl-benzenepropanethiol. A detailed example of this method is provided in Example 5. Detailed examples of applying nanothin polymerization coatings to a gold coated silicon substrate are shown in Examples 6 and 7. Mild polymerization was induced by exposing the crude compound to air at room temperature overnight. The polymer was diluted to 1% w/w in chloroform. This solution was then diluted to the equivalent of 1 mM 4-vinyl-benzenepropanethiol and the substrates were submersed in this solution. It is noted that while hexane was used, any organic solvent may also be used. As shown in FIG. 9, the thickness of the polymerization coating ranged from about 2 nm to 5 nm and could be controlled with time. Further, based upon a phase contrast atomic force microscopy image of a bare-gold substrate, and a 3 nm polymerization coating, the polymerization coating had a smooth texture as shown by analysis. It is further noted that the polymerization coating was resistant to 30 minutes of immersion in hexane, toluene, ethanol, and 1M potassium chloride. Stated another way, the thickness did not significantly changed, as shown in FIG. 10. Also, in terms of stability, the polymerization coating was also resistant to 100 scans from −1.5 volts to −0.5 volts and 0.1 molar sulfuric acid, which readily removes any self-assembled monolayer of dodecanethiol. Thus, as shown in FIG. 11, the polymerization coating was substantially more insulating than the self-assembled monolayer of 1,6-hexanedithiol having a similar thickness.

Evidence of the complete coverage of the metal surface was derived from both structural and functional characterization studies. The structural evidence is most straightforward in Atomic Force Microscopy (AFM) imaging, especially involving polycrystalline metal surfaces. In a representative AFM experiment, random areas of bare metal and coated metal were imaged. Samples of bare metal showed polycrystalline structure with individual crystals of metal averaging 300×300 nm. The polymer-coated sample showed that the polycrystalline structure was completely obscured. The roughness of the polymer-coated surface is identical to the roughness of bare metal proving that the polymer material has a uniform thickness. Ellipsometric measurements of the same sample showed the 3.1 nm thickness of polymer material. These observations conclusively demonstrate the complete coverage of the metal surface by the nanothin polymer coating.

In addition to metal substrates, the technology disclosed herein may also be applied to coat other surfaces. Ellipsometry provided evidence that silicon/silica substrates could be coated with a polymer coating of 63.8±18.8 angstroms after 16 hours. Also, copper substrates, such as a copper penny, were submersed in a polymer solution for 16 hours. The pennies having the polymerization coating did not demonstrate corrosion as did the controlled pennies. Electrochemical data conclusively demonstrate insulating properties of polymer coatings described in the present invention. Corrosion of the copper material was induced by placing it is a solution of bleach overnight (about 24 hours). The copper metal surface that was coated with the polymer described in the present invention, specifically Example 5, did not exhibit signs of corrosion. Control sample that was not coated corroded significantly.

This patent application expressly incorporates by reference all patents, references, and publications disclosed herein.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

EXAMPLES

Example 1

Preparation of p-(3-Bromopropl)acetophenone 1-bromo-3-phenylpropane was purchased from a commercially available source. In a reaction flask 15 g of aluminum chloride was added to 100 mL of methylene chloride. The reaction flask was incubated in a partially submersed ice bath. 5.6 g of acetic anhydride was diluted by adding 5 mL of methylene chloride and then added to the reaction flask during a time period of 30 minutes while under an argon atmosphere. Next, the mixture was stirred for an additional 15 minute period of time. 5 g of 1-bromo-3-phenylpropane was diluted into 5 mL of methylene chloride and then added to the reaction mixture during a 30 period of time while the mixture was under an argon atmosphere. Subsequent to this addition, the mixture was stirred for an additional 2 hours while still in the ice bath. The mixture was then slowly poured onto 200 g of crushed ice, the organic phase was washed with 10% hydrochloric acid (2×100 mL). NaHCO$_3$ (2×100 mL), and sodium chloride 2×100 mL), in that order. The solvent was then removed under a vacuum in order to recover the product.

Example 2

Preparation of p-(3-bromopropyl-a-Methylbenzenemethanol

The product retrieved from Example 1 is used as a starting material in this preparation. That product from Example 1 was diluted into 60 mL of methynol. While that product was in a reaction flask that was submersed in an ice bath and also under argon atmosphere, 0.75 g of sodium borohydride was added during a 5 minute period of time. Subsequent to the addition, the mixture was stirred for an additional 2 hours while still over an ice bath. At that point, 100 mL of water was added to the mixture and the resulting product was extracted with methylene chloride. The solvent was removed under a vacuum in order to allow recovery of the product.

Example 3

Preparation of p-(3-Bromopropyl)styrene

The product from Example 2 is used as a stating material in this procedure. The resulting product from Example 2 was diluted in 200 mL of toluene. Next, 0.125 g of toluensulfonic acid was added to the reaction mixture. The reaction mixture was refluxed under argon atmosphere for 44 hours. The mixture was then washed with 50 mL of water and the solvent was removed under vacuum. The resulting product was then purified by silica gel chromatography with the use of 90% hexane and 10% ethyl acetate. The resulting product was recovered as the solvent was removed under vacuum.

Example 4

Preparation of 4-Vinylbenzenepropanethiol

The product resulting from Example 3 was diluted into 200 mL of methynol, then 5 g of thiourea was added to this solution which was allowed to gently reflux for 16 hours. Thereafter, 15 mL of 12% sodium hydroxide was added and the mixture was allowed to reflux for 4 hours. Next, 20 mL of methylene chloride was added and 10 normal sulfuric acid was added dropwise until the pH dropped to 9.5. Thereafter, 100 mL of water was added to the mixture and the product was extracted with methylene chloride. The product was recovered as the solvent was removed under vacuum.

Example 5

Method of Applying 4-Vinylbenzenepropanethiol Monolayer to Gold

A gold coated silicon substrate was submersed in a 1 mM solution of 4-vinylbenzenepropanethiol at room temperature for two hours. The substrate was then removed from the solution and submersed into a separate container of tetrahydrofuran for 10 seconds. The substrate was removed from the tetrahydrofuran solution and was then rinsed with water. The substrate was immediately blown dry in a stream of argon.

Example 6

Method of Applying 4-Vinylbenzenepropanethiol Oligomers to Gold

A gold coated silicon substrate was submersed in a 1 mM solution of oligomerized 4-vinylbenzenepropanethiol at room temperature for two hours. The substrate was then removed from the solution and submersed into a separate container of tetrahydrofuran for 10 seconds. The substrate was removed from the tetrahydrofuran solution and was then rinsed with water. The substrate was immediately blown dry in a stream of argon.

Example 7

Method of Applying 4-Vinylbenzenepropanethiol to Gold with Controlled Thickness

A gold coated silicon substrate was submersed in a 1 mM solution of 4-vinylbenzenepropanethiol at room temperature for one hour. The container holding the substrate within the solution was placed in a Rayonet ultraviolet photochemical cabinet equipped with two, 35 watt, 253.7 nm lamps. The lid was removed from the container and the ultraviolet lamps were turned on for 30 minutes. The substrate was then removed from the solution and submersed into a separate container of tetrahydrofuran for 10 seconds. The substrate was removed from the tetrahydrofuran solution and was then rinsed with water. The substrate was immediately blown dry in a stream of argon. The above procedure was repeated up to four times to control the thickness of the coating between about one and five nanometers.

What is claimed is:

1. A compound having the formula:

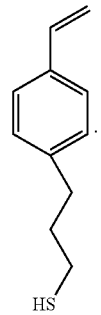

2. A polymer of the compound of claim 1.

3. The polymer of claim 2, wherein the polymer has a thickness of from about 1 to about 10 nanometers.

4. A method of applying a compound to a metal, comprising:
   providing 4-vinylbenzenepropanethiol as a solution in an organic solvent;
   providing a metal;
   placing the metal in the solution of 4-vinylbenzenepropanethiol so that the solution is in contact with the metal surface;
   exposing the mixture to ultraviolet radiation.

5. The method of claim 4, wherein exposing the mixture to ultraviolet radiation further comprises exposing the mixture to ultraviolet radiation having a wavelength of from about 200 nanometers to about 300 nanometers for a duration of from about 10 minutes to about 1 hour.

6. The method of claim 5, wherein exposing the mixture to ultraviolet radiation further comprises exposing the mixture to ultraviolet radiation having a wavelength of about 255 nanometers for a duration of from about 10 minutes to about 1 hour.

7. The method of claim 6, wherein the metal is selected from a group consisting of copper, gold, platinum, and iron.

8. A method of applying a compound to a metal, comprising:
   providing 4-vinylbenzenepropanethiol;
   providing a metal in hexane;
   placing the 4-vinylbenzenepropanethiol in the hexane with the metal in order to prepare a mixture;
   adding a thermal free radical initiator such as benzoyl peroxide to the mixture;
   incubating the mixture at from about 50 degrees Celsius to about 90 degrees Celsius.

9. The method of claim 8, wherein the incubating mixture further comprises incubating for from about 15 minutes to about 24 hours.

10. The method of claim 8, wherein the thermal free radical initiator is benzoyl peroxide.

11. A method of applying a compound to a metal, comprising:
    providing 4-vinylbenzenepropanethiol;
    exposing the 4-vinylbenzenepropanethiol to air at room temperature for from about 30 minutes to about 24 hours;
    diluting the 4-vinylbenzenepropanethiol and its oligomers in an organic solvent to about 1% w/w;

contacting the metal with the solution of 4-vinylbenzenepropanethiol and its oligomers.

12. The method of claim 11, further comprising incubating the metal in the solution of 4-vinylbenzenepropanethiol for from about 10 seconds to about 40 hours.

13. The method of claim 12, wherein incubating the metal in the solution of 4-vinylbenzenepropanethiol is from about 10 seconds to about 30 minutes.

14. A method of making 4-vinylbenzenepropanethiol, comprising:

provinding 1-bromo-3-phenylpropane adding acetic anhydride and aluminum chloride;

incubating the mixture at from about −20 to about 20 degrees Celsius for from about 1 hour to about 12 hours;

isolating the resulting p-(3-bromopropyl)acetophenone;

adding sodium borohydride to the p-(3-bromopropyl)acetophenone solution in methanol;

incubating the mixture at about 0 degrees Celsius for about 2 hours;

isolating the resulting p-(3-bromopropyl)-α-methylbenzenemethanol;

adding toluensulfonic acid to the solution of p-(3-bromopropyl)-α-methylbenzenemethanol in toluene;

refluxing the mixture under inert atmosphere for about 4 hours;

isolating the resulting p-(3-Bromopropyl)styrene;

adding thiourea to the p-(3-Bromopropyl)styrene;

gently refluxing the mixture for about 16 hours;

adding sodium hydroxide;

gently refluxing the mixture for about 4 hours.

\* \* \* \* \*